US010364253B2

(12) United States Patent
Appajosyula et al.

(10) Patent No.: US 10,364,253 B2
(45) Date of Patent: Jul. 30, 2019

(54) SALINOMYCIN DERIVATIVES AND THERAPEUTIC USES THEREOF

(71) Applicant: Channel Therapeutics, Inc., Boca Raton, FL (US)

(72) Inventors: Sireesh Appajosyula, Raleigh, NC (US); Kandalam V. Ramanujachary, Glassboro, NJ (US); Subash C. Jonnalagadda, Glassboro, NJ (US)

(73) Assignee: Channel Therapeutics, Inc., Boca Raton, FL (US)

( * ) Notice: Subject to any disclaimer, the term of this patent is extended or adjusted under 35 U.S.C. 154(b) by 0 days.

(21) Appl. No.: 15/753,160

(22) PCT Filed: Aug. 15, 2016

(86) PCT No.: PCT/US2016/046997
§ 371 (c)(1),
(2) Date: Feb. 15, 2018

(87) PCT Pub. No.: WO2017/031038
PCT Pub. Date: Feb. 23, 2017

(65) Prior Publication Data
US 2018/0230163 A1  Aug. 16, 2018

Related U.S. Application Data

(60) Provisional application No. 62/206,047, filed on Aug. 17, 2015.

(51) Int. Cl.
| | | |
|---|---|---|
| *C07D 493/20* | (2006.01) | |
| *A61P 35/00* | (2006.01) | |
| *A61K 45/06* | (2006.01) | |
| *A61K 31/35* | (2006.01) | |
| *A61K 31/4409* | (2006.01) | |
| *A61K 31/496* | (2006.01) | |

(52) U.S. Cl.
CPC ............ *C07D 493/20* (2013.01); *A61K 31/35* (2013.01); *A61K 31/4409* (2013.01); *A61K 31/496* (2013.01); *A61K 45/06* (2013.01); *A61P 35/00* (2018.01)

(58) Field of Classification Search
CPC ....... C07D 493/20; A61P 35/00; A61K 31/35; A61K 31/4409; A61K 31/496; A61K 45/06

USPC ....................................................... 514/254.1
See application file for complete search history.

(56) References Cited

PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Antoszczak, Michal et al., 'Synthesis and antiproliferative activity of new bioconjugates of Salinomycin with amino acid esters', Bioorganic & Medicinal Chemistry Letters, E-Pub. Jul. 2, 2015, vol. 25, pp. 3511-3514.
Stefanska, Joanna et al., 'Tertiary amides of Salinomycin: A new group of antibacterial agents against Bacillus anthracis and methicillin-resistant *Staphylococcus epidermidis*', Bioorganic & Medicinal Chemistry Letters, E-Pub. Apr. 4, 2015, vol. 25, pp. 2082-2088.
Huczynski, Adam et al., 'Synthesis and antimicrobial activity of amide derivatives of polyether antibiotic-salinomycin', Bioorganic & Medicinal Chemistry Letters, E-Pub. May 26, 2012, vol. 22, pp. 4697-4702.
Antoszczak, Michal et al., 'Synthesis, antiproliferative and antibacterial activity of new amides of salinomycin', Bioorganic & Medicinal Chemistry Letters, E-Pub. Feb. 25, 2014, vol. 24, pp. 1724-1729.
Huang, Xiaoli et al., 'Semisynthesis of SY-1 for Investigation of Breast Cancer Stem Cell Selectivity of C-Ring-Modified Salinomycin Analogues', ACS Chemical Biology, E-Pub. May 19, 2014, vol. 9, pp. 1587-1594.
International Search Report in International application No. PCT/US2016/046997, dated Nov. 21, 2016.

* cited by examiner

*Primary Examiner* — Kristin A Vajda
(74) *Attorney, Agent, or Firm* — Knobbe, Martens, Olson & Bear, LLP

(57) ABSTRACT

The invention relates to salinomycin derivatives such as compounds having the structure of formula (I) or a pharmaceutically acceptable salt thereof, pharmaceutical compositions comprising a therapeutically effective amount of compounds of formula (I), and the use of compounds of formula (I) for treating or inhibiting progression of cancer. The cancer is selected from the group consisting of breast cancer, pancreatic cancer, and prostate cancer.

25 Claims, 2 Drawing Sheets

SALINOMYCIN DERIVATIVES AND THERAPEUTIC USES THEREOF

INCORPORATION BY REFERENCE TO PRIORITY APPLICATION

The present application is the U.S. National Phase of International Application No. PCT/US2016/046997, filed Aug. 15, 2016 and published on Feb. 23, 2017 as WO 2017/031038, which claims the benefit of priority to U.S. Provisional Patent Application No. 62/206,047, filed Aug. 17, 2015 and entitled Salinomycin Derivatives And Therapeutic Uses Thereof, each of which is hereby expressly incorporated by reference in its entirety.

BACKGROUND

Field

Salinomycin derivatives, methods of making such compounds, pharmaceutical compositions and medicaments comprising such compounds, and methods of using such compounds to treat, prevent, alleviate or diagnose diseases, disorders, or conditions associated with cancers are provided.

Description of the Related Art

Salinomycin (SAL), a polyether antibiotic isolated from *Streptomyces albus*, exhibits high activity against drug-sensitive and drug-resistant bacteria strains. For this reason, SAL is commonly used in veterinary medicine as a non-hormonal and growth promoting agent. However, its activity against Gram-positive bacteria is much stronger than against Gram-negative bacteria. It can be explained by the greater complexity of the cell wall of latter type bacteria, which is impermeable to hydrophobic compounds, like SAL. In addition to the antibacterial activity of SAL it has been also demonstrated in many reports that this antibiotic shows anti-parasitic, including anti-malarial and anti-coccidial, anti-fungal as well as anti-viral, including anti-HIV activity.

SUMMARY

Some embodiments disclosed herein relate to a compound of formula (I) or a pharmaceutically acceptable salt thereof.

or a pharmaceutically acceptable salt thereof, wherein:
X is NR or

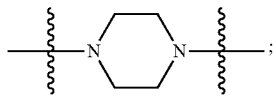 [SMILES: *N1CCN(*)CC1]

R is selected from the group consisting of H, $C_1$-$C_6$ alkyl, $C_2$-$C_6$ alkenyl, $C_2$-$C_6$ alkynyl, $C_1$-$C_6$ heteroalkyl, $C_3$-$C_7$ carbocyclyl, 5-10 membered heterocyclyl, $C_{6-10}$ aryl, and 5-10 membered heteroaryl;

n is an integer from 0 to 6;

Y is selected from the group consisting of —$NR^1C(O)$, —$C(O)NR^1$—, —$OC(O)$—, $C(O)O$—, —$CR^1(COOR^2)$—$CR^3$=$CR^4$—, and —$CR^1$=$CR^2$—;

m is an integer from 0 to 6;

Z is —$CR^1$=$CR^2$—, —$CR^1(COOR^2)$—$CR^3$=$CR^4$, or absent;

G is selected from the group consisting of $C_1$-$C_6$ alkyl, $C_2$-$C_6$ alkenyl, $C_2$-$C_6$ alkynyl, $C_1$-$C_6$ heteroalkyl, $C_3$-$C_7$ carbocyclyl, 5-10 membered heterocyclyl, $C_{6-10}$ aryl, and 5-10 membered heteroaryl, each optionally substituted with 1-3 substituents selected from the group consisting of halogen, $C_{1-4}$ alkyl, halogen$C_{1-4}$ alkyl, —$OR^1$, —$CN$, —$NO_2$, —$NR^1R^2$, —$C(O)NR^1R^2$, and —$NR^1C(O)R^5$; and each of $R^1$, $R^2$, $R^3$, $R^4$, and $R^5$ are independently selected from —H, —CN, —$NO_2$, —$NH_2$, —OH, $C_{1-4}$ alkyl, halogen$C_{1-4}$ alkyl, $C_{2-10}$alkenyl, $C_{2-10}$alkynyl, $C_{3-7}$ cycloalkyl, 3-8 membered heterocyclyl, $C_{6-10}$aryl, and 5-10 membered heteroaryl.

Some embodiments disclosed herein relate to methods of treating cancer, comprising administering a therapeutically effective amount of a compound of formula (I), a compound selected from Table 1, a pharmaceutically acceptable salt thereof, or a pharmaceutical composition thereof to a subject in need thereof. In some such embodiments, the method further comprises identifying the subject as having or at risk of having cancer. In some such embodiments, the cancer is selected from breast cancer, pancreatic cancer, or prostate cancer.

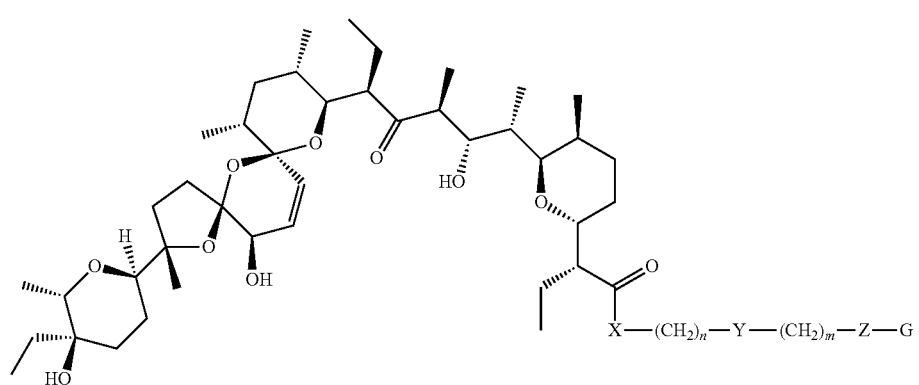

(I)

Figure 2:
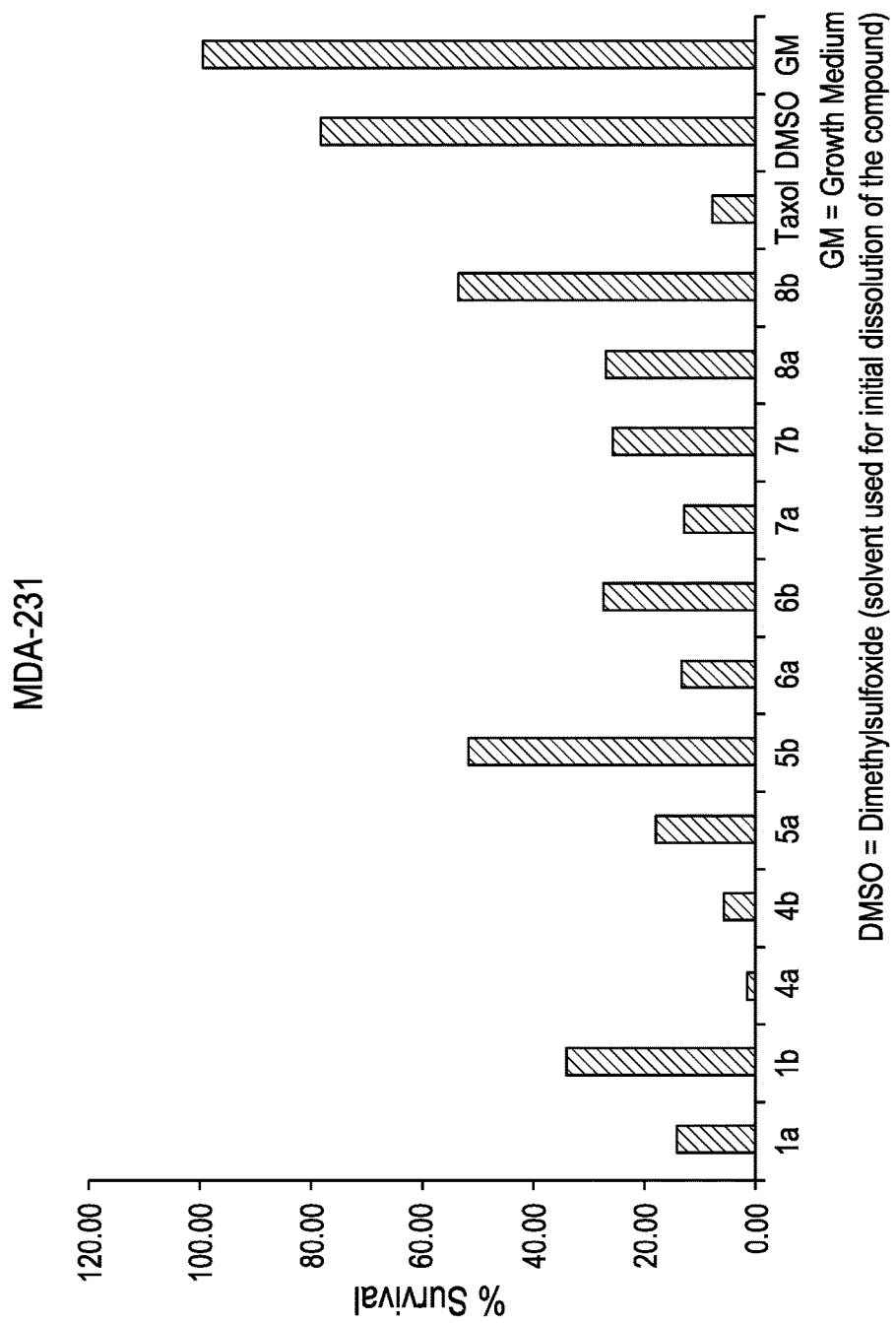

FIG. 2 illustrates the in vitro ($IC_{50}$) Data for SAL derivative compounds 1, 4 to 8 on human breast cancer MDA-MB-231 cell lines.

DETAILED DESCRIPTION OF THE PREFERRED EMBODIMENT

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:

Ac Acetyl
$Ac_2O$ Acetic anhydride
aq. Aqueous
Bn Benzyl
Bz Benzoyl
BOC or Boc tert-Butoxycarbonyl
Bu n-Butyl
cat. Catalytic
° C. Temperature in degrees Centigrade
ee % Enantiomeric excess
Et Ethyl
EtOAc or EA Ethyl acetate
EWG Electron withdrawing group
g Gram(s)
GM Growth medium
h or hr Hour(s)
iPr Isopropyl
LCMS Liquid chromatography-mass spectrometry
m or min Minute(s)
MeOH Methanol
MeCN Acetonitrile
M.P. Melting point
mL Milliliter(s)
PE Petroleum ether
PG Protecting group
Ph Phenyl
rt Room temperature
TEA Triethylamine
Tert, t tertiary
THF Tetrahydrofuran
TLC Thin-layer chromatography
μL Microliter(s)

"Solvate" refers to the compound formed by the interaction of a solvent and a compound described herein or salt thereof. Suitable solvates are pharmaceutically acceptable solvates including hydrates.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)

alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

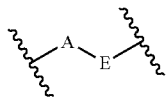

includes the substituent being oriented such that the A is attached at the leftmost attachment point of the molecule as well as the case in which A is attached at the rightmost attachment point of the molecule.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

A therapeutic effect relieves, to some extent, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Compounds

Some embodiments disclosed herein relate to a compound of formula (I) as described above or a pharmaceutically acceptable salt thereof.

In some embodiments, X is NR. In some embodiments, X is

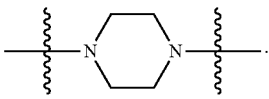

In some embodiments, R is H. In some embodiments, R is $CH_3$.

In some embodiments, n is 0. In some embodiments, n is 2. In some embodiments, n is 4.

In some embodiments, Y is —NR¹C(O) or —C(O)NR¹—. In some embodiments, Y is —OC(O)— or C(O)O—. In some embodiments, Y is —CR¹=CR²—. In some embodiments, Y is —CR¹(COOR²)—CR³=CR⁴—. In some embodiments, R¹ is H.

In some embodiments, m is 0. In some embodiments, m is 1. In some embodiments, m is 3.

In some embodiments, Z is —CR¹=CR²—. In some embodiments, when Z is —CR¹=CR²—, each of R¹ and R² are independently H or CN. In some embodiments, Z is C(CN)=CH. In some embodiments, Z is —CR¹(COOR²)—CR³=CR⁴. In some embodiments, when Z is —CR¹(COOR²)—CR³=CR⁴, each of R¹, R², R³, and R⁴ are H or C$_{1-4}$ alkyl. In some embodiments, when Z is —CR¹(COOR²)—CR³=CR⁴, R¹, R³, and R⁴ are H, and R² is CH₃. In some embodiments, Z is absent.

In some embodiments, G is C$_{6-10}$ aryl optionally substituted with 1-3 substituents selected from the group consisting of halogen, C$_{1-4}$ alkyl, halogenC$_{1-4}$ alkyl, —OR¹, —CN, —NO₂, —NR¹R², —C(O)NR¹R², and —NR¹C(O)R⁵. In some embodiments, G is a phenyl optionally substituted with 1-3 substituents selected from the group consisting of halogen, C$_{1-4}$ alkyl, halogenC$_{1-4}$ alkyl, —OR¹, —CN, —NO₂, —NR¹R², —C(O)NR¹R², and —NR¹C(O)R⁵.

In some embodiments, G is selected from the group consisting of

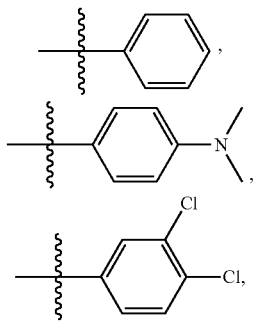

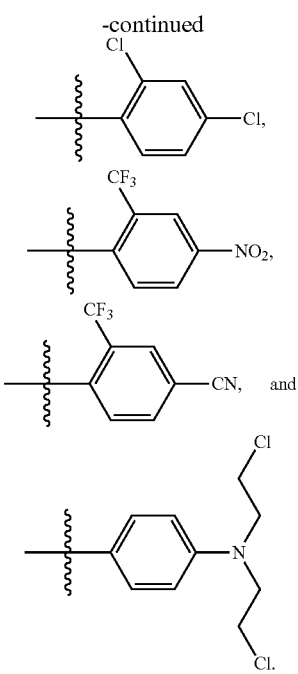

In some embodiments, G is 5-10 membered heteroaryl optionally substituted with 0-3 substituents selected from the group consisting of halogen, C$_{1-4}$ alkyl, halogenC$_{1-4}$ alkyl, —OR¹, —CN, —NO₂, —NR¹R², —C(O)NR¹R², and —NR¹C(O)R⁵. In some embodiments, G is selected from imidazole, pyrazole, triazole, tetrazole, thiazole, thiadiazole, oxazole, oxadiazole, isoxazole, isothiazole, pyridine, pyrazine, pyrimidine, pyridazine, azetidine, and pyrazine, each optionally substituted with halogen, C$_{1-4}$ alkyl, halogenC$_{1-4}$ alkyl, —OR¹, —CN, —NO₂, —NR¹R², —C(O)NR¹R², and —NR¹C(O)R⁵. In some embodiments, G is pyridine.

In some embodiments, the compound of formula (I) has the structure selected from Compounds 1-13, or pharmaceutically acceptable salts thereof.

TABLE 1

| Compd. # | Structure | M.P. (° C.) |
|---|---|---|
| 1 | 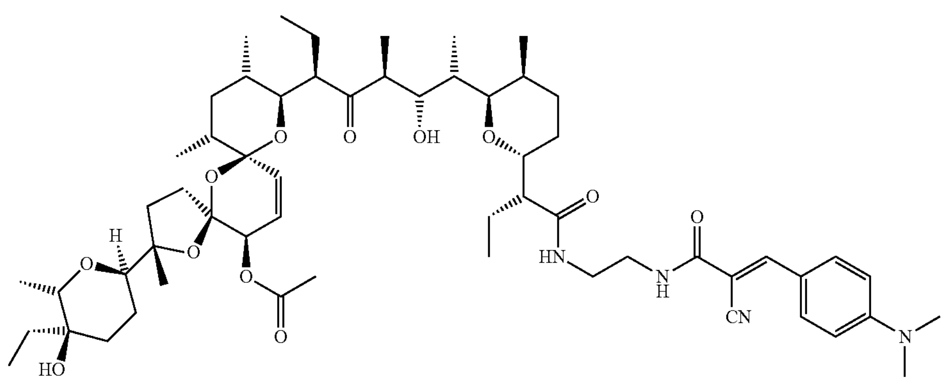 | 100-102 |

TABLE 1-continued
| Compd. # | Structure | M.P. (° C.) |
|---|---|---|
| 4 | 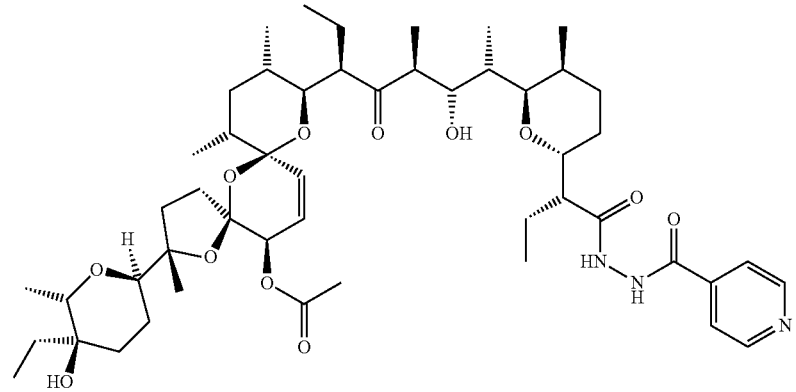 | 191-193 |
| 5 | 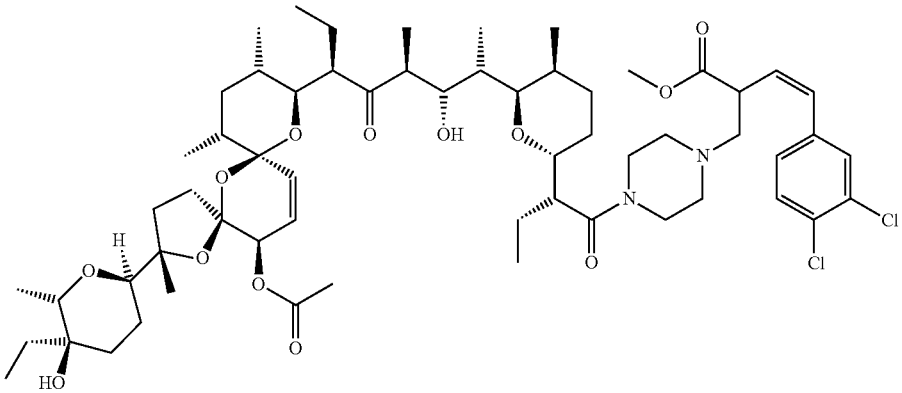 | 98-100 |
| 6 | 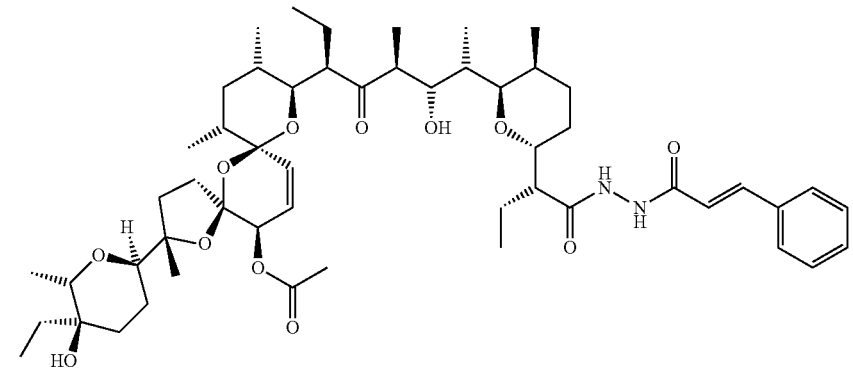 | 223-225 |
| 7 | 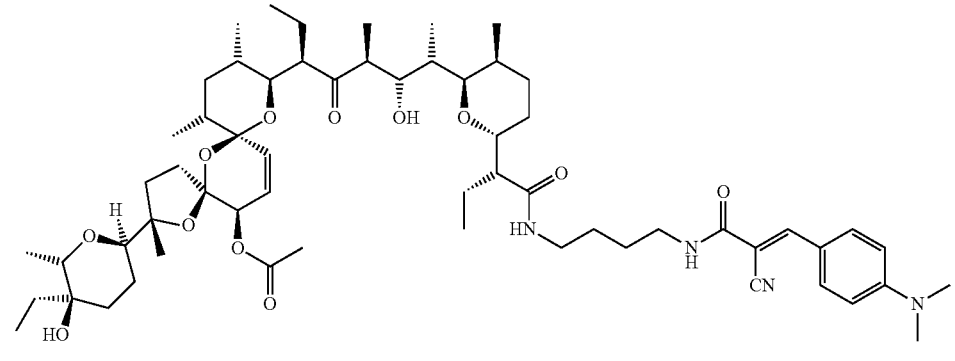 | 104-106 |

TABLE 1-continued
| Compd. # | Structure | M.P. (° C.) |
|---|---|---|
| 8 | 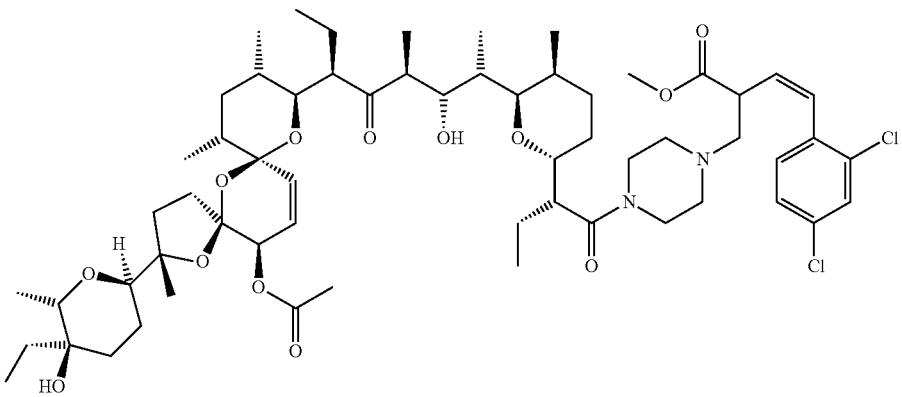 | 112-114 |
| 9 | 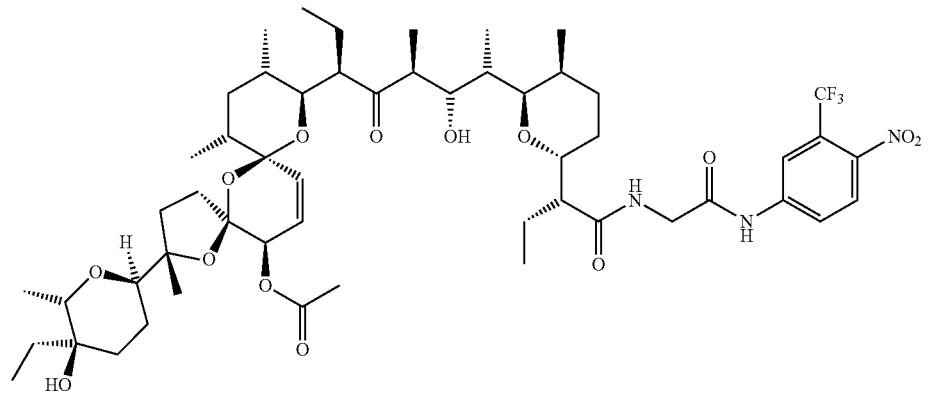 | 136-138 |
| 10 | 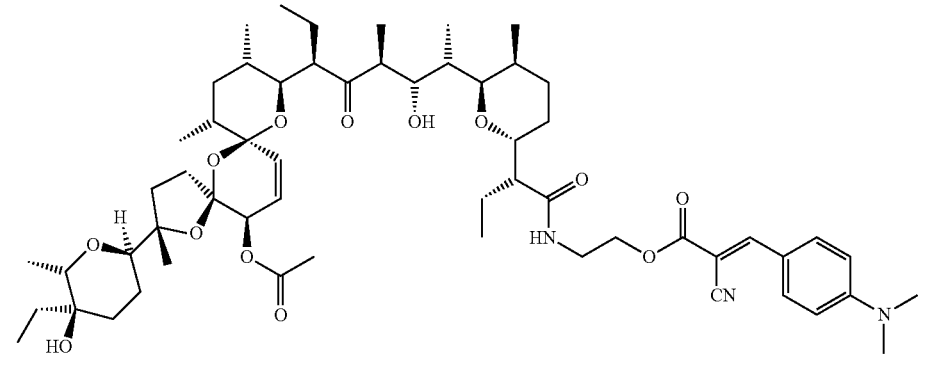 | 174-176 |
| 11 | 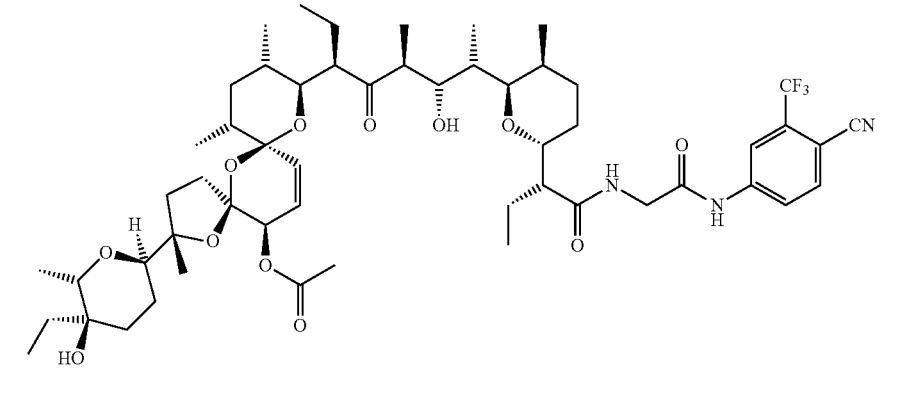 | 109-111 |

TABLE 1-continued

| Compd. # | Structure | M.P. (° C.) |
|---|---|---|
| 12 | 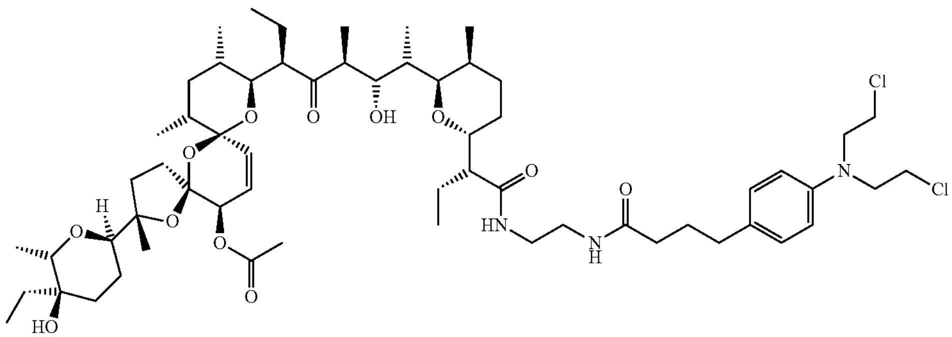 | 110-112 |
| 13 | 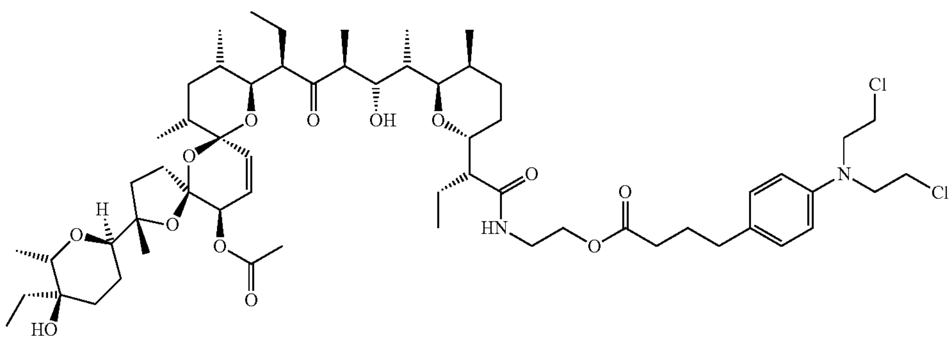 | — |

Administration and Pharmaceutical Compositions

Some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

The compounds are administered at a therapeutically effective dosage, e.g., a dosage sufficient to provide treatment for the disease states previously described. While human dosage levels have yet to be optimized for the compounds of the preferred embodiments, generally, a daily dose for most of the compounds described herein is from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety.

In addition to the selected compound useful as described above, some embodiments include compositions containing a pharmaceutically-acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Method of Treatment

Some embodiments described herein relate to a method of treating or inhibiting progression of cancer, which can include administering a therapeutically effective amount of a compound disclosed herein, or a pharmaceutically acceptable salt thereof, to a subject. The methods include identifying a subject at risk for or having cancer and administering a compound to the subject in an effective amount for therapeutic treatment or prophylactic treatment of cancer. In some embodiments, the cancer is breast cancer. In some other embodiments, the cancer is pancreatic cancer. In some embodiments, the cancer is prostate cancer.

In some embodiments, the subject is a human.

The terms "therapeutically effective amount," as used herein, refer to an amount of a compound sufficient to cure, ameliorate, slow progression of, prevent, or reduce the likelihood of onset of the identified disease or condition, or to exhibit a detectable therapeutic, prophylactic, or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

For any compound, the therapeutically or prophylactically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. However, pharmaceutical compositions that exhibit narrow therapeutic indices are also within the scope of the invention. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In one aspect, treating a condition described herein results in an increase in average survival time of a population of treated subjects in comparison to a population of untreated subjects. Preferably, the average survival time is increased by more than about 30 days; more preferably, by more than about 60 days; more preferably, by more than about 90 days; and even more preferably by more than about 120 days. An increase in survival time of a population may be measured by any reproducible means. In a preferred aspect, an increase in average survival time of a population may be measured, for example, by calculating for a population the average length of survival following initiation of treatment with an active compound. In an another preferred aspect, an increase in average survival time of a population may also be measured, for example, by calculating for a population the average length of survival following completion of a first round of treatment with an active compound.

In another aspect, treating a condition described herein results in a decrease in the mortality rate of a population of treated subjects in comparison to a population of subjects receiving carrier alone. In another aspect, treating a condition described herein results in a decrease in the mortality rate of a population of treated subjects in comparison to an untreated population. In a further aspect, treating a condition described herein results a decrease in the mortality rate of a population of treated subjects in comparison to a population receiving monotherapy with a drug that is not a compound of the embodiments, or a pharmaceutically acceptable salt, metabolite, analog or derivative thereof. Preferably, the mortality rate is decreased by more than about 2%; more preferably, by more than about 5%; more preferably, by more than about 10%; and most preferably, by more than about 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease related deaths per unit time following completion of a first round of treatment with an active compound.

In another aspect, treating a condition described herein results in a reduction in the rate of cellular proliferation. Preferably, after treatment, the rate of cellular proliferation is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating a condition described herein results in a reduction in the proportion of proliferating cells. Preferably, after treatment, the proportion of proliferating cells is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating a condition described herein results in a decrease in size of an area or zone of cellular proliferation. Preferably, after treatment, size of an area or zone of cellular proliferation is reduced by at least 5% relative to its size prior to treatment; more preferably, reduced by at least about 10%; more preferably, reduced by at least about 20%; more preferably, reduced by at least about 30%; more preferably, reduced by at least about 40%; more preferably, reduced by at least about 50%; even more preferably, reduced by at least about 60%; and most preferably, reduced by at least about 75%. Size of an area or zone of cellular proliferation may be measured by any reproducible means of measurement. In a preferred aspect, size of an area or zone of cellular proliferation may be measured as a diameter or width of an area or zone of cellular proliferation.

The methods described herein may include identifying a subject in need of treatment. In a preferred embodiment, the methods include identifying a mammal in need of treatment. In a highly preferred embodiment, the methods include identifying a human in need of treatment. Identifying a subject in need of treatment may be accomplished by any means that indicates a subject who may benefit from treatment. For example, identifying a subject in need of treatment may occur by clinical diagnosis, laboratory testing, or any other means known to one of skill in the art, including any combination of means for identification.

As described elsewhere herein, the compounds described herein may be formulated in pharmaceutical compositions, if desired, and can be administered by any route that permits treatment of the disease or condition. A preferred route of administration is oral administration. Administration may take the form of single dose administration, or the compound of the embodiments can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

Combination Therapy

Further embodiments include administering a combination of compounds to a subject in need thereof. A combination can include a compound, composition, pharmaceutical composition described herein with an additional medicament. In some embodiments, the additional medicament is a chemotherapeutic agent. In some embodiments, the additional chemotherapeutic agent can be an antineoplastic agent. Examples of the antineoplastic agents include but are not limited to paclitaxel, docetaxel, doxorubicin, etoposide, carboplatin, cisplatin, topotecan, gemcitabine, tamoxifen, 5-fluorouracil, adriamycin, daunorubicin, vincristine, nedaplatin, oxaliplatin, satraplatin, triplatin, tetranitrate, and vinblastine.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In some embodiments, the agents are administered simultaneously. In some such embodiments, administration in combination is accomplished by combining the agents in a single dosage form. In some embodiments, the agents are administered sequentially. In some embodiments the agents are administered through the same route, such as orally. In some other embodiments, the agents are administered through different routes, such as one being administered orally and another being administered i.v. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Synthesis

The compounds disclosed herein may be synthesized by methods described below, or by modification of these methods. Ways of modifying the methodology include, among others, temperature, solvent, reagents etc., known to those skilled in the art. Additional embodiments are disclosed in further detail in the following examples, which are not in any way intended to limit the scope of the claims.

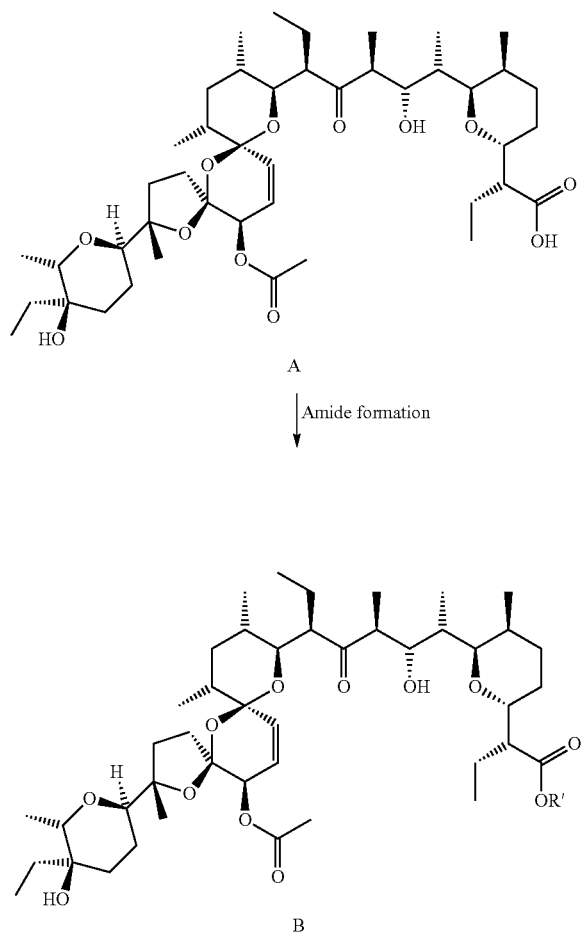

Scheme 1. Synthesis of Salinomycin derivative

The carboxylic acid group of Compound A (Salinomycin acid form) can react with an amine, piperazine, or hydrazine to form an amide bond to produce Compound B. Method for preparing of salinomycin derivative can be found in Huczynski A et al., *Bioorganic & Medicinal Chemistry Letters* 22 (2012) 4697-4702; Huczynski A et al., *Bioorganic & Medicinal Chemistry Letters* 22 (2012) 7146-7150; Antoszczak M, et al., *Bioorganic & Medicinal Chemistry Letters* 24 (2014) 1724-1729; Antoszczak M, et al., *European Journal of Medicinal Chemistry* 76 (2014) 435e444; Borgstrom B, et al., *Chem. Commun.*, 2013, 49, 9944; and Huang X et al., *ACS Chem Biol.* 2014 Jul. 18; 9(7):1587-94, and Stefańska J. et al., *Bioorganic & Medicinal Chemistry Letters*, 25(10), May 2015, 2082-2088.

EXAMPLES

Procedure A: Peptide Coupling of Salinomycin with Amines

To a stirred solution of Salinomycin sodium salt (1.0 equiv.) in dichloromethane at 0° C., was added diisopropylethylamine (2.0 equiv.), HoBt (1.1 equiv.), and EDCI (1.1 equiv.) and stirred for 30 min. Then appropriate primary amine (0.9 equiv.) was added in portions and stirred overnight at room temperature. After completion of the reaction as indicated by TLC, quenched with sat. $NaHCO_3$ (10 mL) solution and extracted with dichloromethane (2×20 mL). The combined organic extracts were washed with brine (1×20 mL), and dried over anhydrous $Na_2SO_4$. The dichloromethane was concentrated in vacuo and the crude product was purified on silica gel column chromatography by using ethyl acetate/hexane obtained salinomycin amides (54-67% yields).

Procedure B: Peptide Coupling of Salinomycin with Piperazines

To a stirred solution of Salinomycin sodium salt (1.0 equiv.) in dichloromethane/N,N'-dimethylformamide (5:1) at 0° C., was added diisopropylethylamine (2.0 equiv.), TBTU (1.1 equiv.), and stirred for 30 min. Then secondary amine (2.0 equiv.) was added in portions and stirred overnight at room temperature. Upon completion (TLC), the solvent was removed under reduced pressure, washed with sat. $NaHCO_3$ (10 mL) solution and organic layer extracted with dichloromethane (2×20 mL). The combined organic extracts were thoroughly washed with cold water (2×10 mL), brine (1×20 mL), and dried over anhydrous $Na_2SO_4$. The dichloromethane was concentrated in vacuo and the crude product was purified on silica gel column chromatography by using ethyl acetate/hexane obtained salinomycin amides.

Procedure C: Peptide Coupling of Salinomycin with Hydrazines

To a stirred solution of SANa (1.0 equiv.) in N,N'-dimethylformamide at 0° C., was added diisopropylethylamine (2.0 equiv.), HoBt (1.1 equiv.), and EDCI (1.1 equiv.) and stirred for 30 min. Then isonicotinylhydrazine (1.0 equiv.) was added in portions and stirred overnight at room temperature. Upon completion (TLC), the solvent was removed under reduced pressure, washed with sat. $NaHCO_3$ (10 mL) solution and organic layer extracted with dichloromethane (2×20 mL). The combined organic extracts were thoroughly washed with cold water (2×10 mL), brine (1×20 mL), and dried over anhydrous $Na_2SO_4$. The dichloromethane was concentrated in vacuo and the crude product was purified on silica gel column chromatography by using ethyl acetate/hexane obtained N,N'-diacylhydrazines.

Example 1

Compound 1 was prepared using Procedure A described above with a yield of 58% as a pale yellow solid.

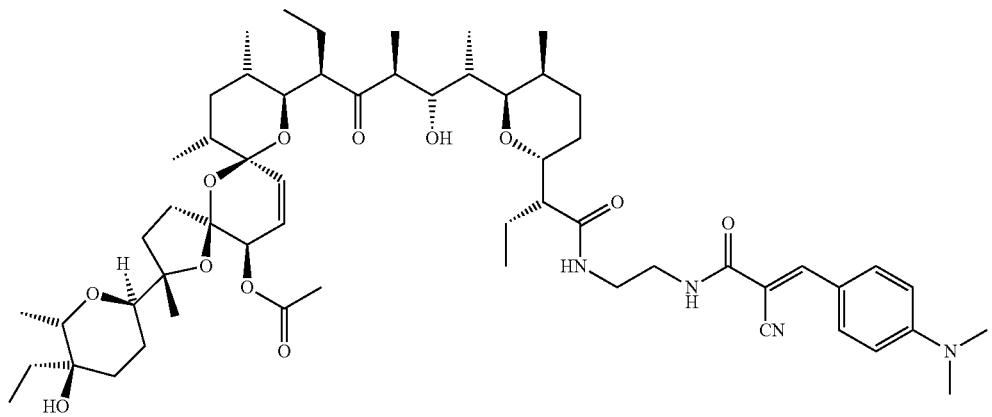

¹H-NMR (CDCl3, 400 MHz): δ 8.00 (s, 1H), 7.95 (m, 1H), 7.86 (d, J=8.0 Hz, 2H), 7.75 (m, 1H), 6.66 (d, J=8.8 Hz, 2H), 6.26 (d, J=3.6 Hz, 1H), 6.23 (d, J=3.2 Hz, 1H), 4.40 (m, 2H), 4.06 (d, J=17.2 Hz, 1H), 3.94-3.86 (m, 3H), 3.76 (m, 2H), 3.64-3.56 (m, 4H), 3.08 (s, 1H), 3.03 (s, 6H), 2.98-2.92 (m, 2H), 2.68 (m, 1H), 2.59 (d, J=8.4 Hz, 1H), 2.29 (m, 1H), 2.15 (m, 1H), 1.98-0.62 (m, 52H);

¹³C-NMR (CDCl$_3$, 100 MHz): δ 214.3, 175.6, 158.9, 154.9, 153.8, 134.3, 133.2, 120.9, 119.4, 117.6, 111.8, 106.5, 99.1, 93.6, 88.4, 79.7, 75.5, 74.4, 71.7, 70.9, 69.8, 67.6, 55.9, 50.5, 49.4, 47.5, 40.6, 40.2, 38.9, 36.7, 33.5, 32.1, 30.9, 30.5, 29.9, 29.5, 29.3, 28.5, 26.7, 26.0, 22.9, 22.7, 22.3, 20.8, 19.3, 17.7, 15.8, 14.8, 14.6, 13.4, 12.1, 11.8, 8.2, 6.5;

ESI-MS: m/z, 1013 [M+Na]⁺.

Example 2

Compound 4 was prepared using Procedure C described above with a yield of 78% as a white solid.

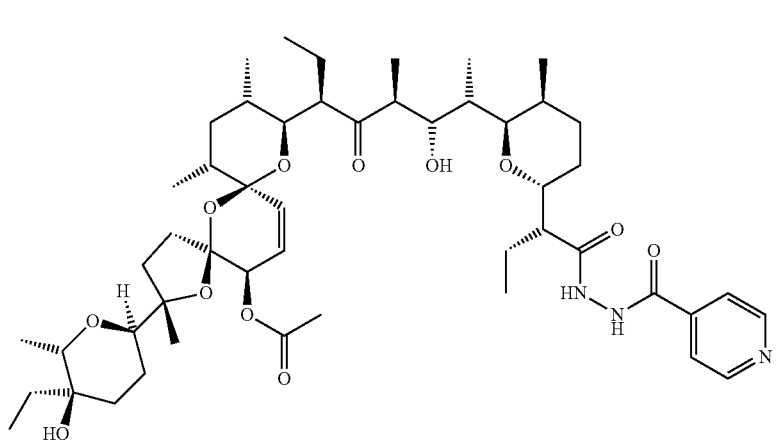

¹H-NMR (CDCl$_3$, 400 MHz): δ 9.85 (s, 1H), 8.72 (m, 3H), 8.09 (d, J=4.4 Hz, 2H), 6.16 (d, J=10.4 Hz, 1H), 6.02 (d, J=10.8 Hz, 1H), 4.37 (m, 1H), 4.15-4.07 (m, 2H), 3.94-3.84 (m, 3H), 3.71 (d, J=9.6 Hz, 1H), 3.58 (d, J=11.6 Hz, 1H), 3.03 (m, 1H), 2.85 (m, 1H), 2.52-2.45 (m, 3H), 2.30 (m, 1H), 2.10-0.88 (m, 47H), 0.79 (d, J=7.2 Hz, 3H), 0.73 (d, J=6.0 Hz, 3H);

¹³C-NMR (CDCl$_3$, 100 MHz): δ 214.6, 174.6, 163.9, 150.4, 139.8, 133.9, 121.9, 120.4, 106.4, 99.0. 90.0, 80.1, 77.0, 75.2, 74.8, 71.2, 71.1, 68.0, 67.0, 52.3, 45.8, 45.6, 40.3, 38.2, 37.1, 36.4, 32.4, 31.0, 30.1, 29.2, 28.2, 26.7, 26.0, 22.2, 22.1, 20.0, 17.2, 16.3, 16.0, 15.2, 15.1, 15.0, 12.2, 11.0, 8.1, 6.6;

ESI-MS: m/z, 892 [M+Na]⁺

Example 3

Compound 5 was prepared using Procedure B described above with a yield of 66% as a white amorphous solid.

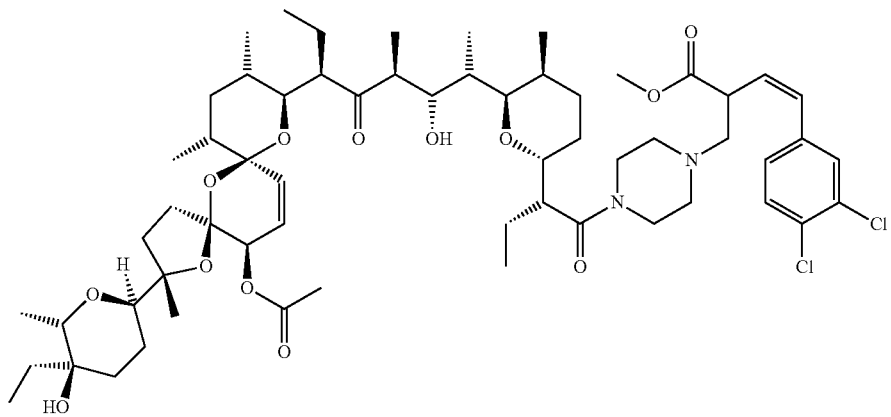

5

¹H-NMR (CDCl₃, 400 MHz): δ 8.10 (s, 1H), 7.78 (s, 1H), 7.53 (m, 1H), 7.47 (m, 1H), 6.04 (d, J=10.4 Hz, 1H), 5.95 (d, J=10.8 Hz, 1H), 4.17 (m, 1H), 3.98-3.88 (m, 3H), 3.81 (s, 3H), 3.78 (m, 2H), 3.60 (m, 4H), 3.29 (m, 3H), 3.02 (m, 1H), 2.79 (m, 4H), 2.79 (m, 1H), 2.52-2.45 (m, 1H), 2.40 (m, 4H), 2.21-0.88 (m, 47H), 0.79 (d, J=7.2 Hz, 3H), 0.73 (d, J=6.0 Hz, 3H);

¹³C-NMR (CDCl₃, 100 MHz): δ 215.4, 172.8, 168.5, 141.9, 135.4, 133.4, 133.3, 132.9, 130.9, 130.6, 130.5, 130.1, 120.8, 106.5, 99.2, 106.5, 99.2, 88.1, 80.1, 76.9, 74.4, 74.2, 73.5, 70.9, 67.8, 53.3, 52.7, 52.6, 52.3, 47.9, 47.1, 46.0, 42.1, 40.6, 38.9, 38.8, 36.9, 36.6, 33.5, 32.1, 30.8, 30.5, 29.9, 29.6, 29.3, 25.9, 23.0, 22.9, 22.3, 17.6, 15.8, 14.7, 14.3, 13.3, 12.5, 8.1, 6.5;

ESI-MS: m/z, 1061 [M+H]⁺.

Example 4

Compound 6 was prepared using Procedure C described above with a yield of 73% as a white amorphous solid.

¹H-NMR (CDCl₃, 400 MHz): δ 9.61 (s, 1H), 8.22 (s, 1H), 7.67 (d, J=15.6 Hz, 1H), 7.48 (d, J=3.6 Hz, 2H), 7.30 (brs, 3H), 6.85 (d, J=16.0 Hz, 1H) 6.10 (d, J=10.4 Hz, 1H), 5.97 (d, J=10.8 Hz, 1H), 4.18 (m, 1H), 4.09-4.01 (m, 2H), 3.89-3.78 (m, 3H), 3.63 (d, J=9.2 Hz, 1H), 3.55 (d, J=9.6 Hz, 1H), 3.01 (m, 1H), 2.74 (m, 1H), 2.52-2.42 (m, 3H), 2.29 (m, 1H), 2.10-0.86 (m, 47H), 0.76 (d, J=6.8 Hz, 3H), 0.68 (d, J=5.6 Hz, 3H);

¹³C-NMR (CDCl₃, 100 MHz): δ 214.7, 174.3, 164.9, 141.3, 135.4, 133.8, 129.7, 129.0, 128.0, 120.5, 119.4, 106.4, 98.9, 89.9, 80.3, 76.8, 75.2, 74.8, 71.4, 71.2, 68.1, 66.7, 52.8, 46.5, 45.9, 40.4, 38.4, 37.1, 36.7, 32.4, 30.9, 30.2, 29.2, 28.3, 26.7, 26.2, 22.3, 22.1, 19.7, 17.3, 16.9, 15.9, 15.2, 14.9, 14.8, 12.2, 10.8, 8.1, 6.6;

ESI-MS: m/z, 917 [M+Na]⁺.

Example 5

Compound 7 was prepared using Procedure A described above with a yield of 54% as a pale yellow solid.

6

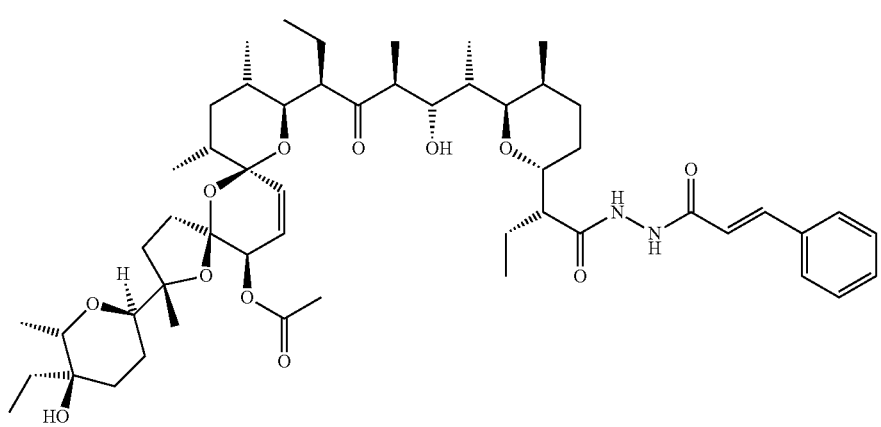

7

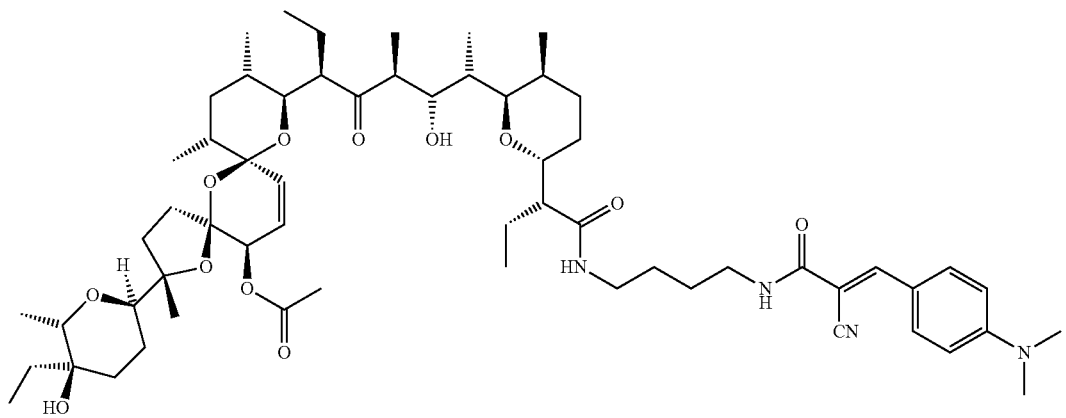

¹H-NMR (CDCl₃, 400 MHz): δ 8.00 (s, 1H), 7.95 (m, 1H), 7.86 (d, J=8.0 Hz, 2H), 7.75 (m, 1H), 6.66 (d, J=8.8 Hz, 2H), 6.26 (d, J=3.6 Hz, 1H), 6.23 (d, J=3.2 Hz, 1H), 4.40 (m, 2H), 4.06 (d, J=17.2 Hz, 1H), 3.94-3.86 (m, 3H), 3.76 (m, 2H), 3.64-3.56 (m, 4H), 3.08 (s, 1H), 3.03 (s, 6H), 2.98-2.92 (m, 2H), 2.68 (m, 1H), 2.59 (d, J=8.4 Hz, 1H), 2.29 (m, 1H), 2.15 (m, 1H), 1.98-0.62 (m, 52H);

¹³C-NMR (CDCl₃, 101 MHz): δ 214.3, 175.6, 158.9, 154.9, 153.8, 134.3, 133.2, 120.9, 119.4, 117.6, 111.8, 106.5, 99.1, 93.6, 88.4, 79.7, 75.5, 74.4, 71.7, 70.9, 69.8, 67.6, 55.9, 50.5, 49.4, 47.5, 40.6, 40.2, 38.9, 36.7, 33.5, 32.1, 30.9, 30.5, 29.9, 29.5, 29.3, 28.5, 26.7, 26.0, 22.9, 22.7, 22.3, 20.8, 19.3, 17.7, 16.5, 16.0, 15.8, 14.8, 14.6, 13.4, 12.1, 11.8, 8.2, 6.5;

ESI-MS: m/z, 1041 [M+Na]⁺.

¹H-NMR (CDCl₃, 400 MHz): δ 7.94 (d, J=7.6 Hz, 1H), 7.84 (s, 1H), 7.36 (s, 1H), 7.28 (d, J=8.4 Hz, 1H), 5.98 (d, J=10.8 Hz, 1H), 5.90 (d, J=10.8 Hz, 1H), 4.17 (m, 1H), 3.98-3.88 (m, 3H), 3.81 (s, 3H), 3.78 (m, 2H), 3.60 (m, 4H), 3.29 (m, 3H), 3.02 (m, 1H), 2.79 (m, 4H), 2.79 (m, 1H), 2.52-2.45 (m, 1H), 2.40 (m, 4H), 2.21-0.88 (m, 47H), 0.79 (d, J=7.2 Hz, 3H), 0.73 (d, J=6.0 Hz, 3H);

¹³C-NMR (CDCl₃, 101 MHz): δ 215.7, 172.8, 168.5, 140.1, 135.4, 133.4, 133.3, 132.9, 130.9, 130.6, 130.5, 130.1, 120.8, 106.5, 99.2, 106.5, 99.2, 88.1, 80.1, 76.9, 74.4, 74.2, 73.5, 70.9, 67.8, 53.3, 52.7, 52.6, 52.3, 47.9, 47.1, 46.0, 42.1, 40.6, 38.9, 38.8, 36.9, 36.6, 33.5, 32.1, 30.8, 30.5, 29.9, 29.6, 29.3, 25.9, 23.0, 22.9, 22.3, 17.6, 15.8, 14.7, 14.3, 13.3, 12.5, 8.1, 6.5;

ESI-MS: m/z, 1061 [M+H]⁺.

Example 6

Compound 8 was prepared using Procedure B described above with a yield of 62% as a white amorphous solid.

Example 7

Compound 9 was prepared using Procedure A described above with a yield of 67% as a white amorphous solid.

8

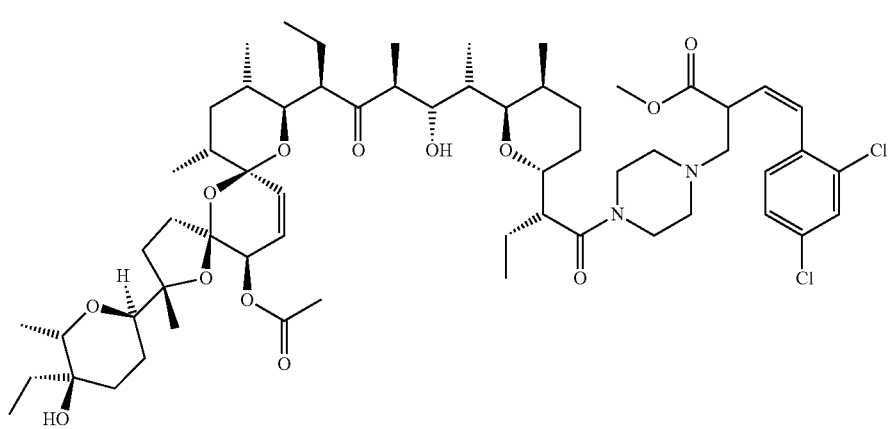

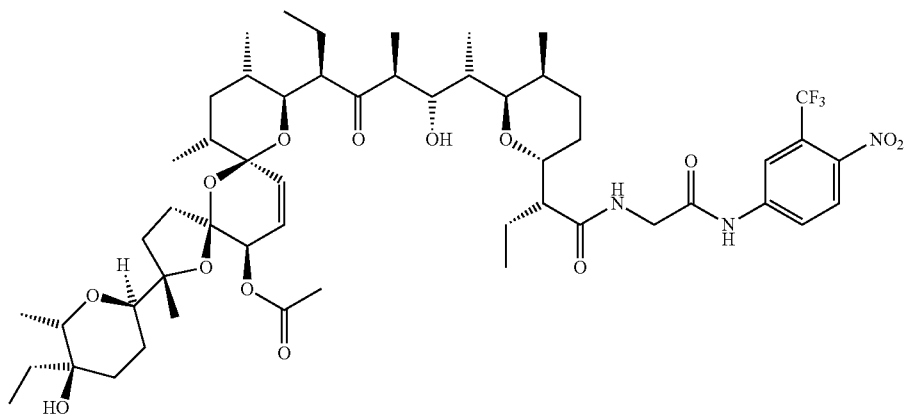

9

¹H-NMR (CDCl₃, 400 MHz): δ 9.89 (s, 1H), 8.17 (d, J=8.8 Hz, 1H), 7.98 (s, 1H), 7.93 (d, J=8.4 Hz, 1H), 7.37 (brs, 1H), 6.13 (d, J=10.4 Hz, 1H), 6.04 (d, J=10.4 Hz, 1H), 4.44-4.29 (dq, J=17.2, 4.8 Hz, 1H), 4.10-3.98 (m, 3H), 3.79 (m, 2H), 3.70 (d, J=10.4 Hz, 1H), 3.57 (d, J=9.2 Hz, 1H), 3.10 (d, J=5.2 Hz, 1H), 2.94-2.84 (m, 2H), 2.53 (d, J=8.8 Hz, 1H), 2.45 (brs, 1H), 2.31 (m, 1H), 2.15 (m, 1H), 1.98-0.72 (m, 52H);

¹³C-NMR (CDCl₃, 100 MHz): δ 214.2, 176.6, 169.1, 143.1, 142.7, 133.3, 127.3, 125.2(q), 123.4, 121.9, 121.6, 120.5, 118.0, 106.8, 99.1, 88.9, 79.0, 76.7, 74.7, 72.1, 70.9, 68.9, 67.0, 54.1, 48.7, 47.2, 45.2, 40.4, 38.6, 37.2, 36.5, 32.8, 30.8, 30.6, 29.2, 28.2, 26.7, 26.2, 22.9, 22.2, 21.9, 20.7, 17.5, 15.9, 14.8, 14.3, 14.1, 12.2, 11.4, 7.9, 6.5;

ESI-MS: m/z, 1018 [M+Na]⁺.

Example 8

Compound 10 was prepared using Procedure A described above with a yield of 59% as a yellow solid.

¹H-NMR(CDCl₃, 400 MHz): δ 7.98 (s, 1H), 7.84 (d, J=7.6 Hz, 2H), 6.68 (brs, 1H), 6.60 (d, J=7.6 Hz, 2H), 6.02 (d, J=10.8 Hz, 1H), 5.90 (d, J=10.0 Hz, 1H), 4.40 (m, 2H), 4.06 (d, J=17.2 Hz, 1H), 3.94-3.86 (m, 3H), 3.76 (m, 2H), 3.64-3.56 (m, 4H), 3.08 (s, 1H), 3.03 (s, 6H), 2.98-2.92 (m, 2H), 2.68 (m, 1H), 2.59 (d, J=8.4 Hz, 1H), 2.29 (m, 1H), 2.15 (m, 1H), 1.98-0.62 (m, 52H);

¹³C-NMR (CDCl₃, 100 MHz): δ 214.3, 175.6, 164.4, 154.9, 153.8, 134.3, 133.2, 120.9, 119.4, 117.6, 111.8, 106.5, 99.1, 93.6, 88.4, 79.7, 75.5, 74.4, 71.7, 70.9, 69.8, 67.6, 64.9, 55.9, 49.4, 47.5, 40.6, 40.2, 38.9, 36.7, 33.5, 32.1, 30.9, 30.5, 29.9, 29.5, 29.3, 28.5, 26.7, 26.0, 22.9, 22.7, 22.3, 20.8, 19.3, 17.7, 15.8, 14.8, 14.6, 13.4, 12.1, 11.8, 8.2, 6.5;

ESI-MS: m/z, 1014 [M+Na]⁺.

Example 9

Compound 11 was prepared using Procedure A described above with a yield of 62% as a white solid.

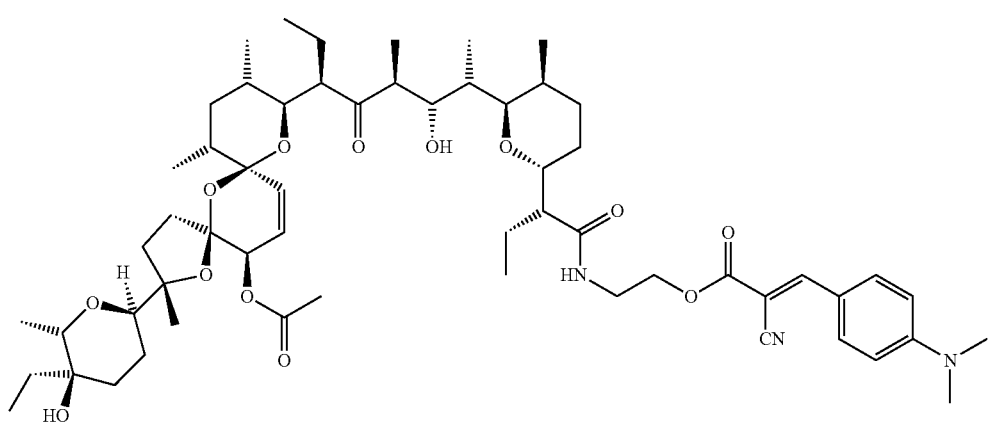

10

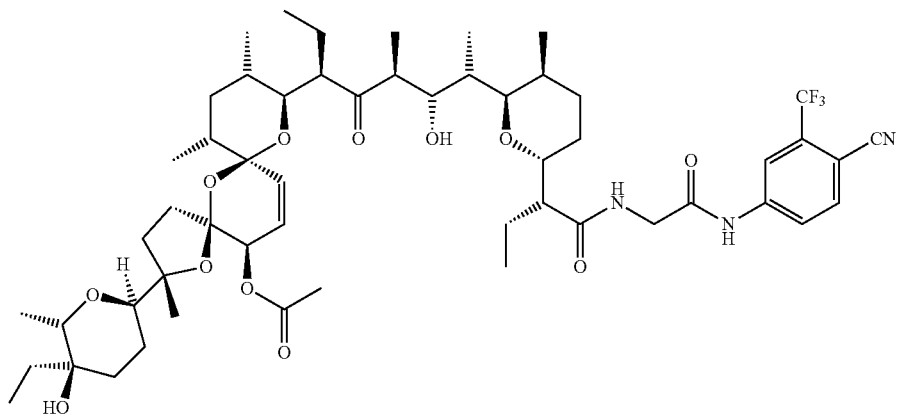
11
¹H-NMR(CDCl₃, 400 MHz): δ 9.80 (s, 1H), 8.10 (d, J=7.6 Hz, 1H), 7.96 (s, 1H), 7.72 (d, J=8.8 Hz, 1H), 7.37 (t, J=4.4 Hz, 1H), 6.13 (d, J=10.8 Hz, 1H), 6.04 (d, J=10.0 Hz, 1H), 4.43-4.29 (dq, J=17.2, 5.6 Hz, 1H), 4.12-3.98 (m, 3H), 3.81 (m, 2H), 3.69 (d, J=10.0 Hz, 1H), 3.56 (d, J=8.8 Hz, 1H), 3.06 (d, J=7.2 Hz, 1H), 2.96-2.83 (m, 2H), 2.52 (d, J=9.2 Hz, 1H), 2.43 (s, 1H), 2.31 (m, 1H), 2.15 (m, 1H), 1.97-0.82 (m, 46H), 0.78 (d, J=6.4 Hz, 3H), 0.72 (d, J=6.8 Hz, 3H);
¹³C-NMR (CDCl₃, 100 MHz): δ 214.7, 176.6, 169.2, 143.0, 135.9, 133.7(q), 133.0, 123.8, 121.8, 121.7, 121.0, 117.2, 115.9, 106.8, 103.6, 99.1, 88.9, 78.7, 76.5, 74.7, 71.9, 70.9, 69.0, 67.1, 54.5, 49.1, 47.6, 44.9, 40.5, 38.6, 37.1, 36.4, 32.9, 30.9, 30.7, 29.2, 28.2, 26.7, 26.2, 22.9, 22.1, 20.7, 17.6, 15.9, 15.2, 14.8, 13.9, 13.9, 12.2, 11.5, 7.9, 6.5;
ESI-MS: m/z, 998 [M+Na]⁺.
Example 10
Compound 12 was prepared using Procedure A described above with a yield of 56% as a pale cream solid.
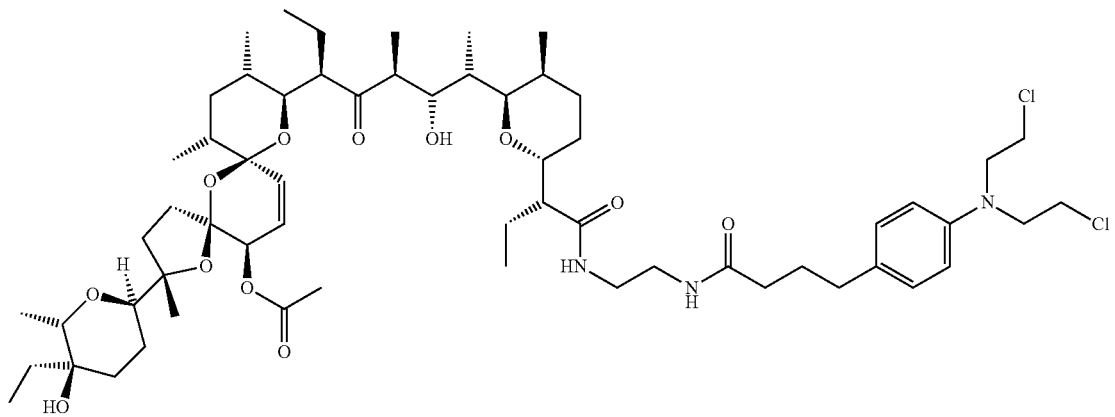
12
¹H-NMR(CDCl₃, 400 MHz): δ 7.62 (m, 1H), 7.05 (d, J=8.4 Hz, 2H), 6.72 (m, 1H), 6.59 (d, J=8.0 Hz, 2H), 6.10 (d, J=10.1 Hz, 1H), 5.98 (d, J=10.9 Hz, 1H), 4.07-4.00 (m, 3H), 3.88-3.59 (m, 14H), 3.47 (d, J=4.7 Hz, 2H), 3.25-3.14 (m, 2H), 3.98 (m, 1H), 2.84 (dt, J=3.9, 11.7 Hz, 1H), 2.71 (m, 1H), 2.40-0.69 (m, 61H);
ESI-MS: m/z, 1100 [M+Na]⁺

Example 11

Compound 13 was prepared using Procedure A described above with a yield of 58% as a colorless solid.

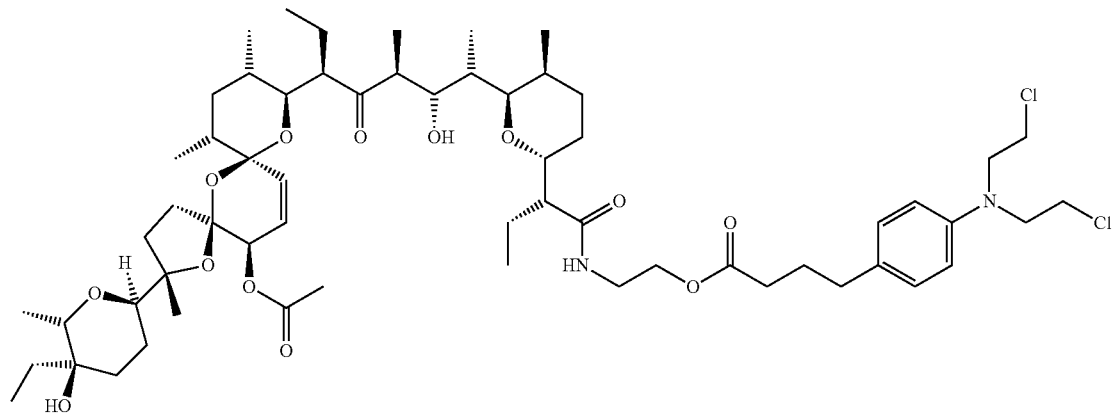

13

$^1$H-NMR(CDCl$_3$, 400 MHz): δ 6.99 (d, J=8.0 Hz, 2H), 6.54 (d, J=8.0 Hz, 2H), 6.52 (m, 1H), 5.98 (d, J=10.1 Hz, 1H), 5.90 (d, J=10.9 Hz, 1H), 4.07-4.00 (m, 3H), 3.88-3.59 (m, 14H), 3.47 (d, J=4.7 Hz, 2H), 3.25-3.14 (m, 2H), 3.98 (m, 1H), 2.84 (dt, J=3.9, 11.7 Hz, 1H), 2.71 (m, 1H), 2.40-0.69 (m, 61H);

ESI-MS: m/z, 1101 [M+Na]$^+$.

Example 12: Cell Viability Assay

After synthesizing the salinomycin derivatives, these molecules were evaluated for their general cytotoxicity against breast cancer cell lines (MDA-MB-231) and pancreatic cancer cell lines (MIAPaCa-2).

Figure 1:
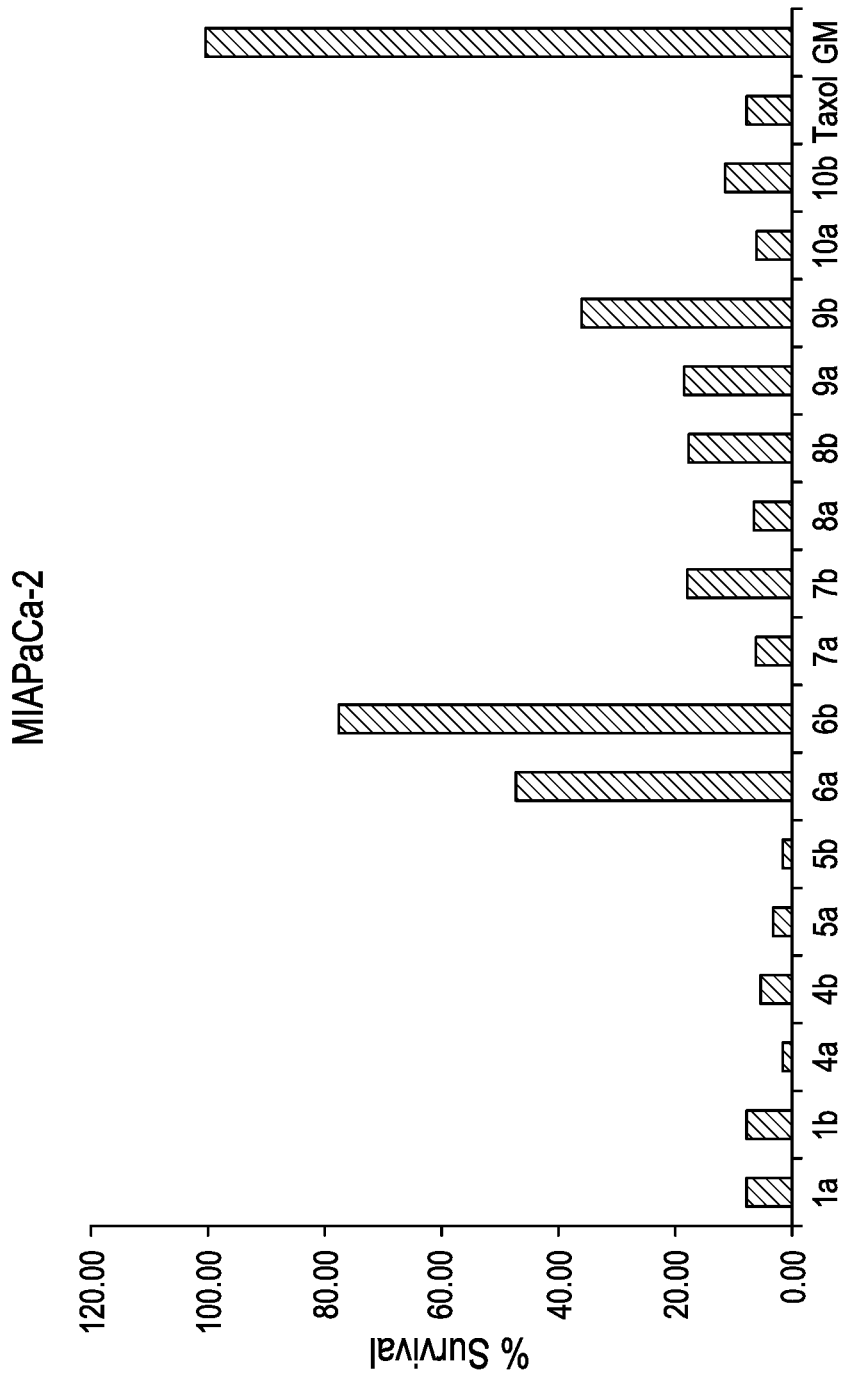
FIG. 1 illustrates the in vitro ($IC_{50}$) Data for SAL derivative compounds 1, 4 to 8 on human pancreatic cancer MIAPaCa-2 cell lines.

Human pancreatic cancer MIAPaCa-2 cells were purchased from ATCC and were maintained in D-MEM supplemented with 10% FBS, 2.5% horse serum, and 1% Penicillin Streptomycin in a humidified atmosphere of 5% CO$_2$ at 37° C. Human breast cancer MDA-MB-231 cells were purchased from ATCC and were maintained in D-MEM supplemented with 10% FBS and 1% Penicillin Streptomycin in a humidified atmosphere of 5% CO$_2$ at 37° C. Cells were seeded in 96 well plates at a density of 5×10$^4$ cells/mL, incubated for 18-24 hours, then exposed to compounds 1-13 at 50 μM and 25 μM concentrations in duplicate for 72 hours. DMSO was added as a negative control. To determine the cell viability, MTT (3-(4, 5-dimethylthiazolyl-2)-2, 5-diphenyltetrazolium bromide) was dissolved in PBS solution (5 mg/mL) and 10 μL was added to each well and incubated. After 4 hours, 100 μL of SDS (sodium dodecyl sulfate) solution (1 g in 10 mL of 0.01 N HCl) was added to solubilize formazan precipitate and incubated for an additional 4 hours. The absorbance of each well was then measured using a microplate reader at 570 nm. The absorbance of control wells was defined as 100% viability and all of the tested compounds were expressed as percentage relative to the control. FIG. 1 shows the in vitro (IC$_{50}$) Data for SAL derivatives 1, 4 to 8 on human pancreatic cancer MIAPaCa-2 cell lines. FIG. 2 shows the in vitro (IC$_{50}$) Data for SAL derivatives 1, 4 to 8 on human breast cancer MDA-MB-231 cell lines. Table 2 shows the activity of the tested compounds against breast cancer cell lines (MDA-MB-231) and pancreatic cancer cell lines (MIAPaCa-2).

TABLE 2

Compound activity against breast cancer cell lines (MDA-MB-231) and pancreatic cancer cell lines (MIAPaCa-2).

| | MIAPaCa | | MDA-MB-231 | |
|---|---|---|---|---|
| Compound # | 50 μM | 25 μM | 50 μM | 25 μM |
| 1 | 8.0 | 8.0 | 14.6 | 34.4 |
| 4 | 1.7 | 5.5 | 1.4 | 6.9 |
| 5 | 3.3 | 1.6 | 18.2 | 51.9 |
| 6 | 47.3 | 77.6 | 13.6 | 27.6 |
| 7 | 6.3 | 17.9 | 13.0 | 25.8 |
| 8 | 6.7 | 17.8 | 27.2 | 53.9 |
| 9 | 18.5 | 36.2 | ND | ND |
| 10 | 6.2 | 11.5 | ND | ND |

While the disclosure has been illustrated and described in detail in the foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:
1. A compound having the structure of Formula (I)

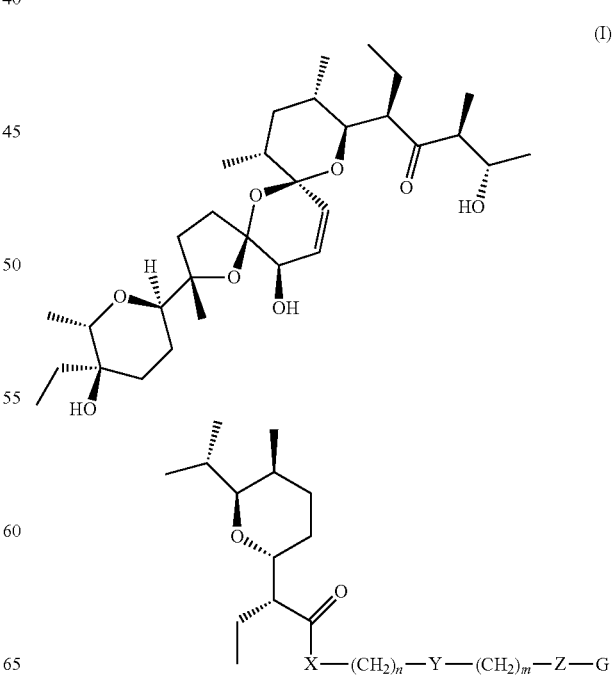

or a pharmaceutically acceptable salt thereof, wherein:
X is

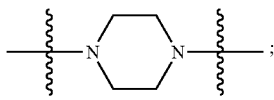

R is selected from the group consisting of H, $C_1$-$C_6$ alkyl, $C_2$-$C_6$ alkenyl, $C_2$-$C_6$ alkynyl, $C_1$-$C_6$ heteroalkyl, $C_3$-$C_7$ carbocyclyl, 5-10 membered heterocyclyl, $C_{6-10}$ aryl, and 5-10 membered heteroaryl;

n is an integer from 0 to 6;

Y is selected from the group consisting of —$NR^1C(O)$—, —$C(O)NR^1$—, —$OC(O)$—, $C(O)O$—, —$CR^1(COOR^2)$—$CR^3$=$CR^4$—, and —$CR^1$=$CR^2$—;

m is an integer from 0 to 6;

Z is —$CR^1$=$CR^2$—, —$CR^1(COOR^2)$—$CR^3$=$CR^4$, or absent;

G is selected from the group consisting of $C_1$-$C_6$ alkyl, $C_2$-$C_6$ alkenyl, $C_2$-$C_6$ alkynyl, $C_1$-$C_6$ heteroalkyl, $C_3$-$C_7$ carbocyclyl, 5-10 membered heterocyclyl, $C_{6-10}$ aryl, and 5-10 membered heteroaryl, each optionally substituted with 1-3 substituents selected from the group consisting of halogen, $C_{1-4}$ alkyl, halogen$C_{1-4}$ alkyl, —$OR^1$, —CN, —$NO_2$, —$NR^1R^2$, —$C(O)NR^1R^2$, and —$NR^1C(O)R^5$; and each of $R^1$, $R^2$, $R^3$, $R^4$, and $R^5$ are independently selected from —H, —CN, —$NO_2$, —$NH_2$, —OH, $C_{1-4}$ alkyl, halogen$C_{1-4}$ alkyl, $C_{2-10}$alkenyl, $C_{2-10}$alkynyl, $C_{3-7}$ cycloalkyl, 3-8 membered heterocyclyl, $C_{6-10}$aryl, and 5-10 membered heteroaryl.

2. The compound of claim 1, wherein R is H or $CH_3$.
3. The compound of claim 1, wherein n is 0, 2, or 4.
4. The compound of claim 1, wherein Y is —$NR^1C(O)$, —$C(O)NR^1$—, —$OC(O)$—, or $C(O)O$—.
5. The compound of claim 4, wherein $R^1$ is H.
6. The compound of claim 1, wherein Y is —$CR^1$=$CR^2$—.
7. The compound of claim 6, wherein $R^1$ is CN and $R^2$ is H.
8. The compound of claim 1, wherein Y is —$CR^1(COOR^2)$—$CR^3$=$CR^4$—.
9. The compound of claim 8, wherein $R^1$, $R^3$, and $R^4$ are H, and $R^2$ is $CH_3$.
10. The compound of claim 1, wherein m is 0, 1, or 3.
11. The compound of claim 1, wherein Z is —$CR^1$=$CR^2$—.
12. The compound of claim 11, wherein each of $R^1$ and $R^2$ are independently H or CN.
13. The compound of claim 12, wherein Z is C(CN)=CH.
14. The compound of claim 1, wherein Z is —$CR^1(COOR^2)$—$CR^3$=$CR^4$.
15. The compound of claim 14, wherein each of $R^1$, $R^2$, $R^3$, and $R^4$ are H or $C_{1-4}$ alkyl.
16. The compound of claim 15, wherein $R^1$, $R^3$, and $R^4$ are H, and $R^2$ is $CH_3$.
17. The compound of claim 1, wherein Z is absent.
18. The compound of claim 1, wherein G is $C_{6-10}$ aryl optionally substituted with 1-3 substituents selected from the group consisting of halogen, $C_{1-4}$ alkyl, halogen$C_{1-4}$ alkyl, —$OR^1$, —CN, —$NO_2$, —$NR^1R^2$, —$C(O)NR^1R^2$, and —$NR^1C(O)R^5$.
19. The compound of claim 18, wherein G is a phenyl optionally substituted with 1-3 substituents selected from the group consisting of halogen, $C_{1-4}$ alkyl, halogen$C_{1-4}$ alkyl, —$OR^1$, —CN, —$NO_2$, —$NR^1R^2$, —$C(O)NR^1R^2$, and —$NR^1C(O)R^5$.

20. The compound of claim 19, wherein G is selected from the group consisting of

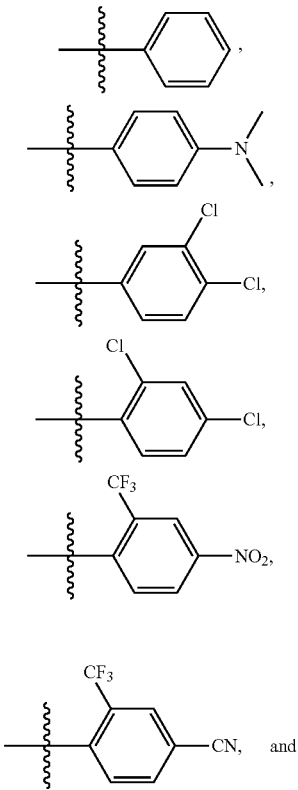

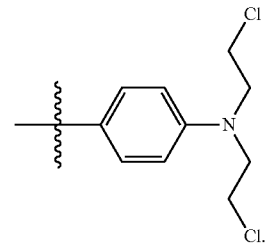

21. The compound of claim 1, wherein G is 5-10 membered heteroaryl optionally substituted with 0-3 substituents selected from the group consisting of halogen, $C_{1-4}$ alkyl, halogen$C_{1-4}$ alkyl, —$OR^1$, —CN, —$NO_2$, —$NR^1R^2$, —$C(O)NR^1R^2$, and —$NR^1C(O)R^5$.

22. The compound of claim 21, wherein G is selected from imidazole, pyrazole, triazole, tetrazole, thiazole, thiadiazole, oxazole, oxadiazole, isoxazole, isothiazole, pyridine, pyrazine, pyrimidine, pyridazine, azetidine, and pyrazine, each optionally substituted with halogen, $C_{1-4}$ alkyl, halogen$C_{1-4}$ alkyl, —$OR^1$, —CN, —$NO_2$, —$NR^1R^2$, —$C(O)NR^1R^2$, and —$NR^1C(O)R^5$.

23. The compound of claim 21, wherein G is pyridine.

24. The compound of claim 1, having a structure selected from the group consisting of:

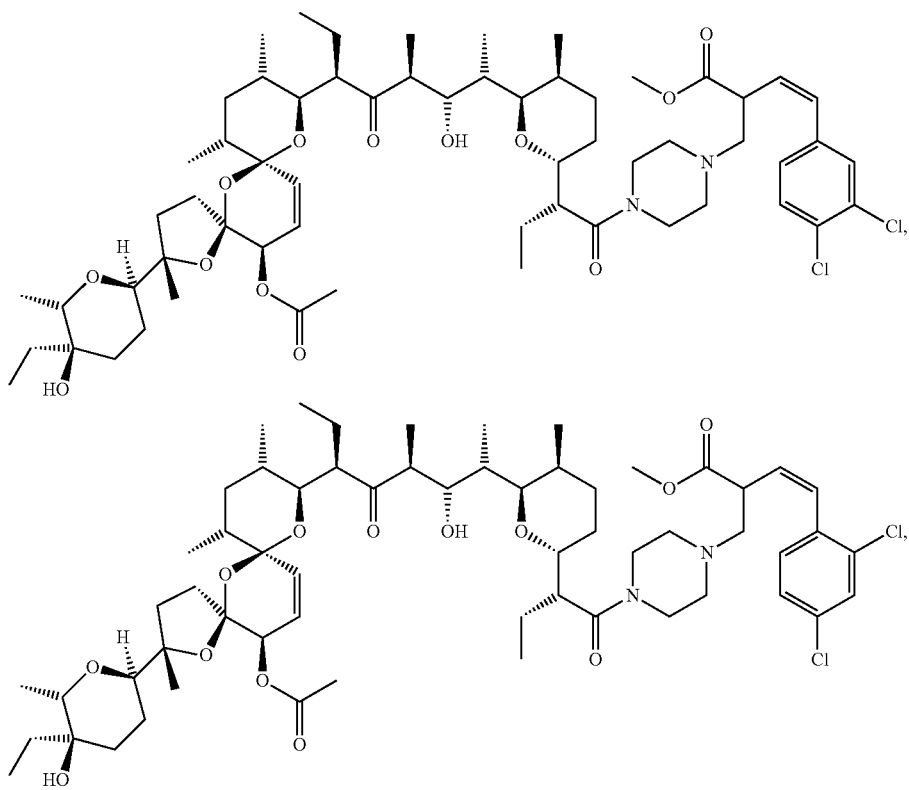
or pharmaceutically acceptable salts thereof.
25. A pharmaceutical composition comprising a therapeutically effective amount of a compound of claim 1 and a pharmaceutically acceptable excipient.
* * * * *